(12) United States Patent
Yabuguchi et al.

(10) Patent No.: US 11,420,184 B2
(45) Date of Patent: Aug. 23, 2022

(54) WATER-ABSORBENT RESIN PARTICLE

(71) Applicant: SUMITOMO SEIKA CHEMICALS CO., LTD., Hyogo (JP)

(72) Inventors: Hiroki Yabuguchi, Himeji (JP); Hiromi Miyashita, Himeji (JP); Hideki Yokoyama, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 362 days.

(21) Appl. No.: 16/499,108

(22) PCT Filed: Mar. 28, 2018

(86) PCT No.: PCT/JP2018/012957
§ 371 (c)(1),
(2) Date: Sep. 27, 2019

(87) PCT Pub. No.: WO2018/181565
PCT Pub. Date: Oct. 4, 2018

(65) Prior Publication Data
US 2020/0038838 A1  Feb. 6, 2020

(30) Foreign Application Priority Data
Mar. 31, 2017  (JP) .............................. JP2017-070908

(51) Int. Cl.
*B01J 20/26*   (2006.01)
*A61L 15/24*   (2006.01)
*A61L 15/60*   (2006.01)
*B01J 20/28*   (2006.01)
*C08F 120/06*  (2006.01)

(52) U.S. Cl.
CPC ............. *B01J 20/267* (2013.01); *A61L 15/24* (2013.01); *A61L 15/60* (2013.01); *B01J 20/28026* (2013.01); *C08F 120/06* (2013.01); *C08F 2810/20* (2013.01)

(58) Field of Classification Search
CPC .... B01J 20/26; B01J 20/267; B01J 20/28026; A61L 15/24; A61L 25/60; C08F 120/06; C08F 2810/20
USPC ........................................................ 502/402
See application file for complete search history.

(56) References Cited

U.S. PATENT DOCUMENTS

| | | |
|---|---|---|
| 4,735,987 A | 4/1988 | Morita et al. |
| 6,284,362 B1 | 9/2001 | Takai et al. |
| 2012/0295103 A1 | 11/2012 | Kikuno et al. |
| 2012/0296299 A1 | 11/2012 | Villanueva et al. |
| 2015/0295103 A1 | 10/2015 | Wolters et al. |

FOREIGN PATENT DOCUMENTS

| | | |
|---|---|---|
| CN | 1461317 | 12/2003 |
| CN | 103272571 | 9/2013 |
| EP | 1291368 | 3/2003 |
| JP | S55-050355 | 4/1980 |
| JP | S62-223203 | 10/1987 |
| JP | S62-254841 | 11/1987 |
| JP | S62-254842 | 11/1987 |
| JP | H5-508425 | 11/1993 |
| JP | 2001-239159 | 9/2001 |
| JP | 2002-035580 | 2/2002 |
| JP | 2005-095759 | 4/2005 |
| JP | 2009-136417 | 6/2009 |
| JP | 2009-142598 | 7/2009 |
| JP | 2011-038102 | 2/2011 |
| JP | 2014-523452 | 9/2014 |
| JP | 2015-503655 | 2/2015 |
| JP | 2016-540106 | 12/2016 |
| WO | 92/000108 | 1/1992 |
| WO | 02/085959 | 10/2002 |
| WO | 2008/015980 | 2/2008 |
| WO | 2011/040530 | 4/2011 |
| WO | 2011/065368 | 6/2011 |
| WO | 2012/053121 | 4/2012 |
| WO | 2012/156346 | 11/2012 |
| WO | 2016/006130 | 1/2016 |

OTHER PUBLICATIONS

International Preliminary Report on Patentability (IPRP) issued in PCT/JP2018/012957, dated Oct. 10, 2019, 8 pages.
Fredric L. Buchholz et al., "Modern Superabsorbent Polymer Technology", 1998, p. 69-103-p. 199-201.
The extended European search report issued for the counterpart European Patent Application No. 18778274.3, dated Oct. 16, 2020, 10 pages.

*Primary Examiner* — Edward M Johnson
(74) *Attorney, Agent, or Firm* — Hamre, Schumann, Mueller & Larson, P.C.

(57) ABSTRACT

Disclosed are water-absorbent resin particles comprising a crosslinked polymer comprising a monomer unit derived from a water-soluble ethylenically unsaturated monomer, wherein an artificial menstrual blood volume increase rate as measured in an artificial menstrual blood swelling test conducted in the order of i), ii), and iii) is 70% or more. i) putting 1.0 g of water-absorbent resin particles into a measuring cylinder with an inner diameter of 27 mm. ii) injecting 10 ml of artificial menstrual blood into the cylinder at once to swell the water-absorbent resin particles. iii) measuring a volume (A) of the swollen water-absorbent resin particles after 60 seconds from the injection and calculating an artificial menstrual blood volume increase rate according to Equation (I) below. Artificial menstrual blood volume increase rate (%)=(A−B)/B×100 . . . (I), A . . . Volume (ml) of swollen water-absorbent resin particles, B . . . Volume (ml) of injected artificial menstrual blood.

5 Claims, 1 Drawing Sheet

(1) (2) (3)
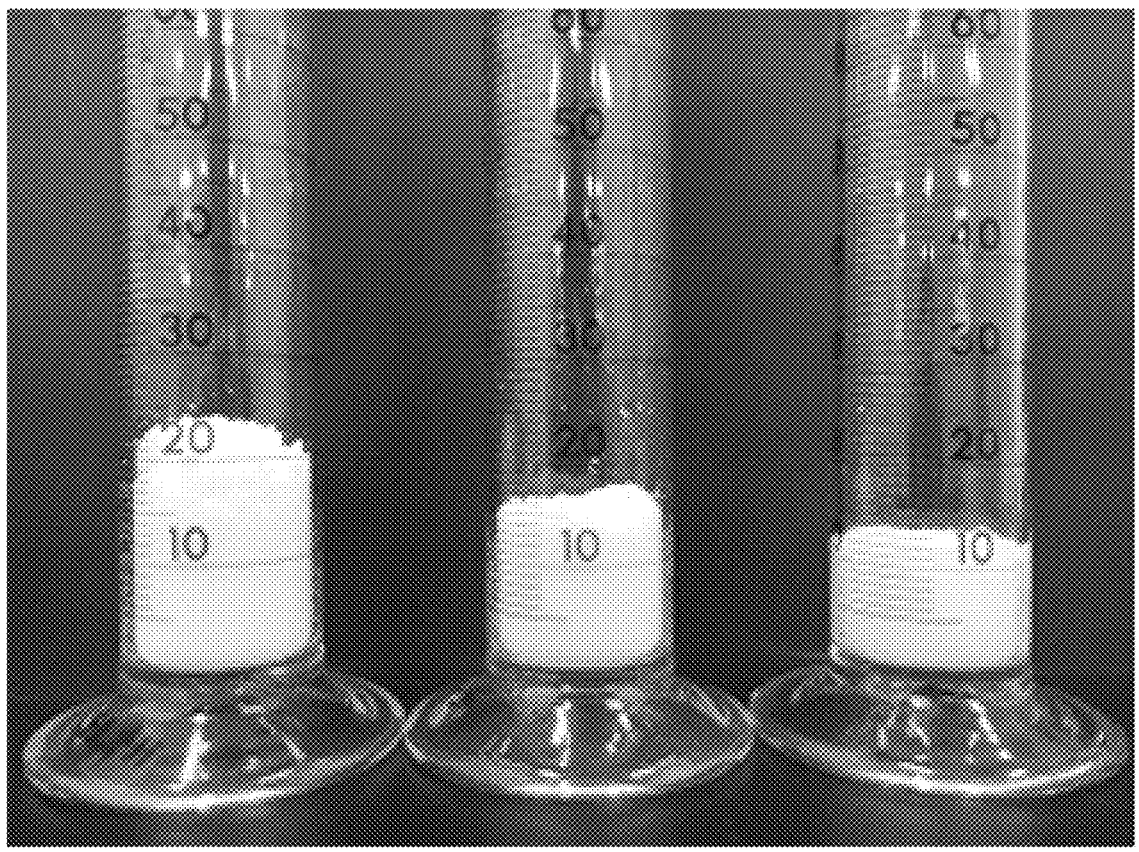

WATER-ABSORBENT RESIN PARTICLE

TECHNICAL FIELD

The present invention relates to water-absorbent resin particles.

BACKGROUND ART

In recent years, a water-absorbent resin has been widely used for various fields, including hygienic materials such as paper diapers and sanitary napkins, agricultural and horticultural materials such as water retaining materials and soil conditioners, industrial materials such as water blocking agents and dew condensation prevention agents, and the like. Among these fields, the water-absorbent resin is more often used for the hygienic materials such as paper diapers and sanitary napkins.

As the water-absorbent resin, for example, a hydrolysate of a starch-acrylonitrile graft copolymer, a neutralized product of a starch-acrylic acid graft copolymer, a saponified product of a vinyl acetate-acrylic acid ester copolymer, and a partially neutralized product of a polyacrylic acid, a hydrolysate of an acrylonitrile copolymer, acrylamide copolymer, or crosslinked products thereof, a crosslinked product of a cationic monomer, or the like is known.

Depending on applications, various liquid absorption characteristics are required for the water-absorbent resin. For example, examples of the characteristics required in the case of the hygienic material application include (1) a high water absorption capacity, (2) a high water retention capacity (performance of keeping moisture in the water-absorbent resin even after dehydration under a certain condition after water absorption), (3) a high water absorption rate, (4) a high gel strength after water absorption, and (5) a reduced amount of the absorbed liquid to return to the outside.

The water-absorbent resin particles used in the field of hygienic materials are usually appropriately crosslinked. For example, with regard to water-absorbent resins that are used in articles mainly intended for absorption of human urine, such as paper diapers and incontinence pads, it is possible to improve liquid absorption characteristics such as a water absorption capacity and a gel strength after water absorption to some extents by controlling a degree of crosslinking.

For the purpose of improving the liquid absorption characteristics of a water-absorbent resin to be applied to blood in particular, several techniques have been proposed. For example, in Patent Literature 1, there is disclosed a technique in which a surface of a water-absorbent resin is treated with an aliphatic hydrocarbon or a specific hydrocarbon compound. In Patent Literature 2, there is disclosed a technique in which a specific water-absorbent resin is coated with alkylene carbonate, and then heated to 150° C. to 300° C. In addition, in Patent Literature 3, there is disclosed a technique in which a water-absorbent resin having a high specific surface area and a high swelling power is used.

CITATION LIST

Patent Literature

[Patent Literature 1] JP S55-50355 A
[Patent Literature 2] JP H05-508425 A
[Patent Literature 3] WO 2002/085959

SUMMARY OF INVENTION

Technical Problem

However, even a water-absorbent resin with a degree of crosslinking controlled has a problem that its liquid absorption characteristics such as a water absorption capacity and a water absorption rate are significantly lowered in a case it targets the blood significantly. The blood is a viscous liquid including protein-containing plasma and solid components such as erythrocytes, leukocytes, and platelets. The water-absorbent resin can absorb an aqueous solution and the like by nature, but cannot absorb the solid components. Therefore, it is considered that in a case where the blood is intended to be absorbed into water-absorbent resin particles, the solid components in the liquid adhere to surfaces of the water-absorbent resin particles to coat the particle surfaces in an early absorption stage, and thus, additional absorption afterwards is disturbed.

Furthermore, the plasma that is a liquid component in the blood includes polymers such as a protein, and since it has a higher viscosity as compared to physiological saline and the like, it is slowly penetrated into water-absorbent resin particles. Accordingly, a phenomenon that some of the water-absorbent resin particles to which are partially first in contact with the viscous liquid are swollen, and the swollen gel disturbs additional passage of the liquid, so-called gel blocking, is likely to occur.

In a case where in order to avoid the gel blocking, for example, a surface of the water-absorbent resin particle is coated with materials including, for example, a hydrophobic material such as an aliphatic hydrocarbon, problems such as an extremely low water absorption rate of the water-absorbent resin particle itself, which thus causes rapid absorption by absorbent materials to be not accomplished, occur. In this regard, it cannot be said that the water-absorbent resin particles treated according to the related art are not necessarily excellent so as to make the blood be absorbed into the inside of the water-absorbent resin particles, whereby there is a further room for improvement.

Therefore, an object of the present invention is to provide water-absorbent resin particles having excellent liquid absorption characteristics with respect to a solid component-containing viscous liquid such as blood, and an absorbent article using the same.

Solution to Problem

The present inventors have newly found that water-absorbent resin particles having excellent liquid absorption characteristics with respect to a solid component-containing viscous liquid can be obtained by increasing the volume after swelling when the water-absorbent resin particles absorb the liquid.

That is, the present invention provides water-absorbent resin particles comprising a crosslinked polymer comprising a monomer unit derived from a water-soluble ethylenically unsaturated monomer, wherein an artificial menstrual blood volume increase rate of 70% or more as measured in an artificial menstrual blood swelling test conducted in the following order of i), ii), and iii).

i) Putting 1.0 g of water-absorbent resin particles into a measuring cylinder with an inner diameter of 27 mm. ii) Injecting 10 ml of artificial menstrual blood into the cylinder at once to swell the water-absorbent resin particles. Measuring a volume (A) of the swollen water-absorbent resin particles after an elapse of 60 seconds from the injection and calculating an artificial menstrual blood volume increase rate according to Equation (I) below.

$$\text{Artificial menstrual blood volume increase rate (\%)} = (A-B)/B \times 100 \quad (I)$$

A . . . Volume (ml) of swollen water-absorbent resin particles

B . . . Volume (ml) of injected artificial menstrual blood

The water-absorbent resin particles can exhibit excellent liquid absorption characteristics with respect to a solid component-containing viscous liquid such as blood.

It is preferable that the water-absorbent resin particles have a ratio of particles having a particle diameter of more than 250 μm and 850 μm or less of 70% by mass or more and a ratio of particles having a particle diameter of 250 μm or less of 20% by mass or less, with respect to the total amount of the water-absorbent resin particles.

It is preferable that the water-absorbent resin particles have an artificial menstrual blood absorption rate of 10 seconds or less.

It is preferable that the water-absorbent resin particles have a water retention capacity of physiological saline of 10 to 25 g/g.

The present invention also provides an absorbent article comprising the water-absorbent resin particles. The absorbent article has an excellent liquid absorbing property for a solid component-containing viscous liquid such as blood.

Advantageous Effects of Invention

According to the present invention, provided are water-absorbent resin particles having excellent liquid absorption characteristics for a solid component-containing viscous liquid such as blood, and an absorbent article using the same.

BRIEF DESCRIPTION OF DRAWINGS

FIG. 1 is a photograph illustrating the results of artificial menstrual blood swelling tests in Examples.

DESCRIPTION OF EMBODIMENTS

Hereinafter, suitable embodiments of the present invention will be described in detail. However, the present invention is not limited to the following embodiments. All configurations described in the present specification can be optionally combined while not departing from the scope of the present invention. For example, numerical value ranges regarding various characteristics can be defined using the upper limit values and the lower limit values of the numerical ranges described in the present specification, or the numerical values optionally selected from the numerical values described in Examples as the upper limit values and the lower limit values.

The water-absorbent resin particles according to the present embodiment comprise a crosslinked polymer comprising a monomer unit derived from a water-soluble ethylenically unsaturated monomer. The water-absorbent resin particles according to the present embodiment have an artificial menstrual blood volume increase rate of 70% or more.

The artificial menstrual blood volume increase rate of the water-absorbent resin particles is measured by an artificial menstrual blood swelling test conducted in the following order of i), ii), and iii). i) Putting 1.0 g of water-absorbent resin particles into a measuring cylinder with an inner diameter of 27 mm. ii) Injecting 10 ml of artificial menstrual blood into the cylinder at once to swell the water-absorbent resin particles. iii) Measuring a volume (A) of the swollen water-absorbent resin particles after an elapse of 60 seconds from the injection and calculating an artificial menstrual blood volume increase rate according to Equation (I) below.

$$\text{Artificial menstrual blood volume increase rate (\%)} = (A-B)/B \times 100 \quad (I)$$

A . . . Volume (ml) of swollen water-absorbent resin particles

B . . . Volume (ml) of injected artificial menstrual blood

More specifically, it can be measured by the method described in Examples which will be described below.

An artificial menstrual blood volume increase rate (60-sec value) of the water-absorbent resin particles according to the present embodiment is, for example, preferably 75% or more, more preferably 80% or more, still more preferably 85% or more, and even still more preferably 90% or more. Further, the artificial menstrual blood volume increase rate of the water-absorbent resin particles may be 95% or more, 100% or more, 110% or more, or 120% or more. In addition, the artificial menstrual blood volume increase rate of the water-absorbent resin particles can be, for example, 200% or less, and may be 150% or less.

An artificial menstrual blood volume increase rate (300-sec value) after an elapse of 300 seconds from the injection of the water-absorbent resin particles according to the present embodiment can be, for example, 90% or more, 100% or more, 110% or more, 120% or more, or 130% or more, and may be 220% or less or 165% or less.

It is considered that the water-absorbent resin particles according to the present embodiment can reduce a gel blocking effect since the volumes and the surface areas of the particles rapidly increase to secure voids that make it possible for a high-viscosity liquid such as blood to be diffused among the water-absorbent resin particles after being brought into contact with the liquid by increasing the artificial menstrual blood volume increase rate. It is also considered that the particles become larger before the particle surfaces are coated with the solid components and the like in the liquid to be absorbed due to the high artificial menstrual blood volume increase rate, and accordingly, it becomes possible for the liquid to be further absorbed into the inside of the particles while not inhibiting the absorption. Therefore, the water-absorbent resin particles according to the present embodiment can exhibit high liquid absorption characteristics even upon liquid absorption after the second test.

It is preferable that the water-absorbent resin particles according to the present embodiment have a ratio of the particles having a particle diameter of more than 250 μm and 850 μm or less of 70% by mass or more and a ratio of the particles having a particle diameter of 250 μm or less of 20% by mass or less, with respect to the total amount of the water-absorbent resin particles. In a case where the water-absorbent resin particles have the same shapes and forms, as the particle diameters are smaller, the specific surface areas become larger, and in this regard, a technique for decreasing a particle diameter in order to increase an absorption rate is known. On the other hand, the water-absorbent resin particles according to the present embodiment having appropriately large particle diameters are preferable since their liquid absorption characteristics with respect to a solid component-containing viscous liquid such as blood are further improved. In addition, in a case where the particle size distribution is within the range, the handleability is improved, which is thus preferable.

The particle size distribution of the water-absorbent resin particles can be measured using sieves having different mesh sizes. In the water-absorbent resin particles according to the present embodiment, a ratio of the particles having a particle diameter of more than 250 μm and 850 μm or less can be 75% or more, or may be 80% by mass or more, 85% by mass or more, or 90% by mass or more, with respect to the total amount of the water-absorbent resin particles. In the water-absorbent resin particles according to the present embodiment, a ratio of particles having a particle diameter of 250 μm or less may be 18% by mass or less, 15% by mass or less, or 10% or less, with respect to the total amount of the water-absorbent resin particles.

The water-absorbent resin particles according to the present embodiment comprise a crosslinked polymer obtained by the polymerization of monomers comprising water-soluble ethylenically unsaturated monomers.

Examples of a method for polymerizing the monomers include a reverse-phase suspension polymerization method, an aqueous solution polymerization method, a bulk polymerization method, and a precipitation polymerization method. Among these, from the viewpoints of making it easy to secure good liquid absorption characteristics of the obtained water-absorbent resin particles and control of the polymerization reaction, the reverse-phase suspension polymerization method or the aqueous solution polymerization method is preferable.

In order to increase the specific surface area of the water-absorbent resin particles, for example, a method in which an anionic surfactant or a nonionic surfactant with a hydrophilic-lipophilic balance (HLB) of 6 or more is used in the reversed-phase suspension polymerization method, a method in which a pyrolyzable foaming agent such as an azo compound is used in an aqueous polymerization, or the like can be adopted. Water-absorbent resin particles obtained by the method in which an anionic surfactant or a nonionic surfactant with an HLB of 6 or more is used in the reversed-phase suspension polymerization method among the above methods can be suitably used. The HLB of the surfactant used in the reverse-phase suspension polymerization is more preferably 6 to 14, and still more preferably 8 to 12.

Hereinbelow, a method of polymerizing water-soluble ethylenically unsaturated monomers will be described by way of an example of the reversed phase suspension polymerization method.

The water-soluble ethylenically unsaturated monomer used in the production of the water-absorbent resin particles according to the present embodiment include (meth)acrylic acid ("acryl" and "methacryl" are hereinafter collectively denoted as "(meth)acryl", and similarly, "acrylate" and "methacrylate" are denoted as "(meth)acrylate") and salts thereof; 2-(meth)acrylamide-2-methylpropanesulfonic acid and salts thereof, (meth)acrylamide, N,N-dimethyl (meth)acrylamide, 2-hydroxyethyl (meth)acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. In a case where the water-soluble ethylenically unsaturated monomer contains an amino group, the amino group may be quaternarized. A functional group such as a carboxyl group and an amino group, which is contained in the monomer, can function as a crosslinkable functional group in a post-crosslinking step which will be described later. These water-soluble ethylenically unsaturated monomers may be used alone or in a combination of two or more kinds thereof.

Among those, at least one compound selected from the group consisting of acrylic acid and a salt thereof, methacrylic acid and a salt thereof, acrylamide, methacrylamide, and N,N-dimethyl acrylamide is preferably included in the water-soluble ethylenically unsaturated monomer, and at least one compound selected from the group consisting of acrylic acid and a salt thereof, methacrylic acid and a salt thereof, acrylamide, is more preferably included, from the viewpoint that they are easily available industrially. At least one compound selected from the group consisting of acrylic acid and a salt thereof, and methacrylic acid and a salt thereof is still more preferably included in the water-soluble ethylenically unsaturated monomer, from the viewpoint of further enhancing the water absorption characteristics.

As the monomer, some of water-soluble monomers other than the above-mentioned water-soluble ethylenically unsaturated monomers may also be used to an extent that exhibition of the effect of the present invention is not inhibited. Such a monomer can be used, for example, in mixture of an aqueous solution including the water-soluble ethylenically unsaturated monomers. An amount of the water-soluble ethylenically unsaturated monomers to be used is preferably 70% to 100 mol % with respect to the total amount of the monomers. In particular, acrylic acid and a salt thereof are more preferably in the amount of 70% to 100 mol % with respect to the total amount of the monomers.

Usually, the water-soluble ethylenically unsaturated monomers are suitably used in the form of an aqueous solution. A concentration of the water-soluble ethylenically unsaturated monomers in an aqueous solution of the water-soluble ethylenically unsaturated monomers (hereinafter referred to as an aqueous monomer solution) may usually be 20% by mass or more and no more than a saturated concentration, and is preferably 25% to 70% by mass, and more preferably 30% to 55% by mass. Examples of water to be used include tap water, distilled water, and ion exchanged water.

In a case where the water-soluble ethylenically unsaturated monomer includes an acid group, the aqueous monomer solution can be used after the acid group is neutralized with an alkaline neutralizing agent. From the viewpoints of increasing the osmotic pressure of the water-absorbent resin particles and further enhancing liquid absorption characteristics such as a water absorption rate, the degree of neutralization in the water-soluble ethylenically unsaturated monomers with an alkaline neutralizing agent is 10% to 100 mol %, preferably 50% to 90 mol %, and more preferably 60% to 80 mol % of the acidic groups in the water-soluble ethylenically unsaturated monomers. Examples of the alkaline neutralizing agent include alkali metal salts such as sodium hydroxide, sodium carbonate, sodium hydrogen carbonate, potassium hydroxide, and potassium carbonate; and ammonia. These alkaline neutralizing agents may be used in a form of an aqueous solution in order to simplify neutralization procedures. The above-mentioned alkaline neutralizing agents may be used alone or in combination of two or more kinds thereof. Neutralization of the acid groups of the water-soluble ethylenically unsaturated monomers can be performed by, for example, adding an aqueous solution of a compound containing an alkaline neutralizing agent such as sodium hydroxide and potassium hydroxide dropwise to the aqueous monomer solution.

In the reverse-phase suspension polymerization method, an aqueous monomer solution is dispersed in a hydrocarbon dispersion medium in the presence of a surfactant, and polymerization of the water-soluble ethylenically unsaturated monomers is performed using a water-soluble radical polymerization initiator or the like. Upon the polymerization, an internal crosslinking agent may be used.

Examples of the surfactant include nonionic surfactants and anionic surfactants. Examples of the nonionic surfactants include sorbitan fatty acid esters, (poly)glycerin fatty acid esters ("(poly)" means both of a case with the prefix "poly" and a case without the prefix "poly", and the same shall apply hereinafter), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymer, polyoxyethylene polyoxypropyl alkyl ethers, and polyethylene glycol fatty acid esters. Examples of the anionic surfactants include fatty acid salts, alkylbenzene sulfonate, alkylmethyl taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. From the viewpoints that the W/O type reverse-phase suspension state is good and water-absorbent resin particles are easily obtained with suitable particle diameters and easily commercially available, it is preferable that the surfactant includes, among those, at least one compound selected from the group consisting of sorbitan fatty acid esters, polyglycerin fatty acid esters, and sucrose fatty acid esters. In addition, from the viewpoint that the liquid absorption characteristics of the obtained water-absorbent resin particles are improved, it is more preferable that the surfactant includes sorbitan fatty acid esters. These surfactants may be used alone or in combination of two or more kinds thereof.

From the viewpoint that the effect with respect to the amount of the surfactant to be used is sufficiently obtained and from the economical viewpoint, the amount of the surfactant to be used is preferably 0.1 to 5 parts by mass, more preferably 0.2 to 3 parts by mass, and still more preferably 0.5 to 2 parts by mass, with respect to 100 parts by mass of the aqueous solution of the water-soluble ethylenically unsaturated monomers.

Examples of the water-soluble radical polymerization initiator include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-methylpropionamidine) dihydrochloride, 2,2'-azobis[2-(N-phenylamidino)propane] dihydrochloride, 2,2'-azobis[2-(N-allylamidino)propane] dihydrochloride, 2,2'-azobis {2-[1-(2-hydroxyethyl)-2-imidazolin-2-yl]propane} dihydrochloride, 2,2'-azobis {2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid). These radical polymerization initiators may each be used alone or in combination of two or more kinds thereof. Further, the water solubility of the water-soluble radical polymerization initiator in the present specification refers to exhibition of a solubility of 5% by mass or more in water at 25° C.

The amount of the water-soluble radical polymerization initiator to be used can be 0.005 to 1 mol with respect to 100 mol of the water-soluble ethylenically unsaturated monomers. In a case where the amount of the radical polymerization initiator to be used is 0.005 mol or more, the polymerization reaction does not require a long period of time, which is thus efficient. In a case where the amount of the radical polymerization initiator to be used is 1 mol or less, there is a tendency that an abrupt polymerization reaction does not occur.

The water-soluble radical polymerization initiator can also be used as a redox polymerization initiator in combination with a reducing agent such as sodium sulfite, sodium hydrogen sulfite, ferrous sulfate, and L-ascorbic acid.

In order to control the liquid absorption characteristics of the water-absorbent resin particles, a chain transfer agent may be included in the aqueous solution of the water-soluble ethylenically unsaturated monomers used for polymerization. Examples of the chain transfer agent include hypophosphites, thiols, thiolic acids, secondary alcohols, and amines.

Examples of a hydrocarbon dispersion medium include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. These hydrocarbon dispersion media may be used alone or in combination of two or more kinds thereof. The hydrocarbon dispersion medium may include at least one compound selected from the group consisting of a chained aliphatic hydrocarbon having 6 to 8 carbon atoms and an alicyclic hydrocarbon having 6 to 8 carbon atoms. From the viewpoints that the W/O type reverse-phase suspension state is good, water-absorbent resin particles having excellent water absorption rates are easily obtained with suitable particle diameters and easily commercially available, and the quality is stabilized, the hydrocarbon dispersion medium may include n-heptane, cyclohexane, or the both. In addition, from the same viewpoint, as a mixture of the hydrocarbon dispersion media, for example, Exxsol Heptane (manufactured by ExxonMobil Chemical: containing 75% to 85% of n-heptane and isomers thereof), which is commercially available, may be used.

From the viewpoint that heat of polymerization is appropriately removed and an easy control over a polymerization temperature is allowed, the amount of the hydrocarbon dispersion medium to be used is preferably 100 to 1,000 parts by mass, more preferably 150 to 800 parts by mass, and still more preferably 200 to 700 parts by mass, with respect to 100 parts by mass of the water-soluble ethylenically unsaturated monomers. With the amount of the hydrocarbon dispersion medium to be used of 100 parts by mass or more, there is a tendency that an easy control over the polymerization temperature is allowed. With the amount of the hydrocarbon dispersion medium to be used of 1,000 parts by mass or less, there is a tendency that the productivity of polymerization is improved, which is economical.

Internal crosslinking occurs by self-crosslinking upon the polymerization. The liquid absorption characteristics of the water-absorbent resin particles may be controlled by carrying out internal crosslinking further using an internal crosslinking agent. Examples of the internal crosslinking agent to be used include compounds having two or more reactive functional groups, such as di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the above polyols with unsaturated acids such as maleic acid and fumaric acid; bis(meth) acrylamides such as N,N'-methylenebis(meth)acrylamide; di- or tri(meth)acrylic acid esters obtained by reacting a polyepoxide with (meth)acrylic acid; carbamyl di(meth) acrylate esters obtained by reacting a polyisocyanate such as tolylene diisocyanate and hexamethylene diisocyanate with hydroxyethyl (meth)acrylate; compounds having two or more polymerizable unsaturated groups, such as allylated starch, allylated cellulose, diallyl phthalate, N,N',N"-triallylisocyanate, and divinylbenzene; polyglycidyl compounds such as (poly)ethylene glycol diglycidyl ether, (poly)glycerin diglycidyl ether, (poly)glycerin triglycidyl ether, (poly) propylene glycol polyglycidyl ether, and polyglycerol polyglycidyl ether; haloepoxy compounds such as epichlorohydrin, epibromohydrin, and α-methyl epichlorohydrin; and isocyanate compounds such as 2,4-tolylene diisocyanate and hexamethylene diisocyanate. These crosslinking agents may be used alone or in combination of two or more kinds thereof.

From the viewpoints that the properties of water solubility are suppressed by appropriately crosslinking of the obtained polymer and sufficient absorption amounts are exhibited, the amount of the internal crosslinking agent is preferably 0 to 0.03 mol, more preferably 0 to 0.01 mol, and still more preferably 0 to 0.005 mol, per mol of the water-soluble ethylenically unsaturated monomer.

Reverse-phase suspension polymerization can be performed in a water-in-oil system by mixing water-soluble ethylenically unsaturated monomers and a water-soluble radical polymerization initiator, and as desired, an internal crosslinking agent, a surfactant, a hydrocarbon dispersion medium, or the like, and heating the mixture under stirring. The order of addition of the respective components and the like can be appropriately adjusted. For example, it is preferable to mix a surfactant with a hydrocarbon dispersion medium in advance, while mix a water-soluble radical polymerization initiator, an internal crosslinking agent, and water-soluble ethylenically unsaturated monomers in advance separately, and mixing these mixed liquids thus each obtained, thereby initiating polymerization. In addition, a multi-stage polymerization method in which the aqueous monomer solution is added multiple times may be used.

A temperature for the polymerization reaction varies depending upon the type of a water-soluble radical polymerization initiator to be used, but from the viewpoints that the reaction is smoothly performed by easily removing heat of polymerization while making the polymerization rapidly proceed and shortening the polymerization time and thus improving economic efficiency, the temperature is preferably 20° C. to 110° C., and more preferably 40° C. to 90° C. The reaction time is usually 0.5 to 4 hours. Termination of the polymerization reaction can be confirmed by, for example, stopping a rise in the temperature within the reaction system. Thus, the water-absorbent resin particles are usually obtained in the state of a hydrous gel.

After the polymerization reaction, the obtained hydrous gel may be subjected to intermediate crosslinking. By the intermediate crosslinking, the degree of crosslinking of the hydrous gel can be increased to improve the liquid absorption characteristics more preferably. The intermediate crosslinking can be carried out by adding a crosslinking agent to the hydrous gel after the polymerization reaction, followed by heating.

Examples of the crosslinking agent for performing the intermediate crosslinking include polyols such as ethylene glycol, propylene glycol, 1,4-butanediol, trimethylolpropane, glycerin, polyoxyethylene glycol, polyoxypropylene glycol, and polyglycerin; compounds having 2 or more epoxy groups, such as (poly)ethylene glycol diglycidyl ether, (poly)propylene glycol diglycidyl ether, and (poly) glycerin diglycidyl ether; haloepoxy compounds such as epichlorohydrin, epibromohydrin, and α-methyl epichlorohydrin; compounds having two or more isocyanate compounds such as 2,4-tolylene diisocyanate and hexamethylene diisocyanate; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these, the polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are preferable. These crosslinking agents may be used alone or in combination of two or more kinds thereof.

From the viewpoints the obtained hydrous gel is appropriately crosslinked, and accordingly, the properties of water solubility are suppressed and good liquid absorption characteristics are exhibited, the amount of the crosslinking agent used for the intermediate crosslinking is preferably 0 to 0.03 mol, more preferably 0 to 0.01 mol, and still more preferably 0 to 0.005 mol, per mol of the water-soluble ethylenically unsaturated monomer.

Subsequently, in order to remove moisture from the obtained hydrous gel, drying is performed. Examples of the drying method include a method (a) in which azeotropic distillation is performed by heating from the outside in the state where the hydrous gel is dispersed in a hydrocarbon dispersion medium, and the hydrocarbon dispersion medium is refluxed to remove moisture, a method (b) in which a polymer in the form of a hydrous gel is taken out by decantation to perform drying under reduced pressure, and a method (c) in which a polymer in the form of a hydrous gel is separated by filtration and dried under reduced pressure. Among those, the method (a) is preferably used due to simplicity in the production step.

Control over the particle diameter of the water-absorbent resin particle can be performed by, for example, adjusting the rotational speed of a stirrer during the polymerization reaction or by adding a powdery inorganic flocculating agent to the system after the polymerization reaction or upon the initiation of drying. There is a tendency that by the addition of the flocculating agent, the particle diameter of the obtained water-absorbent resin particle can be increased. Examples of the powdery inorganic flocculating agent include silica, zeolite, bentonite, aluminum oxide, talc, titanium dioxide, kaolin, clay, and hydrotalcite, and among these, from the viewpoint of the aggregation effect, silica, aluminum oxide, talc, or kaolin is preferable.

In the reverse-phase suspension polymerization, as a method for adding the powdery inorganic flocculating agent, a method in which a powdery inorganic flocculating agent is dispersed in the same type of a hydrocarbon dispersion medium as that for use in the polymerization or water in advance, followed by mixing in a hydrocarbon dispersion medium including a hydrous gel under stirring, is preferable.

The amount of the powdery inorganic flocculating agent to be added is preferably 0.001 to 1 part by mass, more preferably 0.005 to 0.5 parts by mass, and still more preferably 0.01 to 0.2 parts by mass, with respect to 100 parts by mass of the water-soluble ethylenically unsaturated monomers. By setting the amount of the powdery inorganic flocculating agent to be added within the above range, it is easy to obtain water-absorbent resin particles having a desired particle size distribution.

The above-mentioned initial time in drying indicates, for example, a state where a water content of the hydrous gel is 50% by mass or more in the drying step after the polymerization reaction. A specific time point for adding the powdery inorganic flocculating agent according to the present embodiment is preferably a time point at which the water content of the hydrous gel is 50% by mass or more, more preferably a time point at which the water content of the hydrous gel is 55% by mass or more, and still more preferably a time point at which the water content of the hydrous gel is 60% by mass or more.

The water content of the hydrous gel is calculated by the following equation.

Water content=($Ww$)÷($Ww$+$Ws$)×100[% by mass]

$Ww$: An amount of moisture in a hydrous gel calculated by adding an amount of moisture used, as desired, upon mixing a powdery inorganic flocculating agent, a post-crosslinking agent, and the like to an amount obtained by subtracting an amount of moisture extracted out to the outside by the drying step from an amount of moisture included in the aqueous liquid before polymerization in the entire polymerization step.

$Ws$: A solid fraction calculated from amounts of materials to be introduced such as water-soluble ethylenically unsaturated monomers which constitute the hydrous gel polymer, a crosslinking agent, and an initiator.

In a certain step of the drying step or later in the production of the water-absorbent resin particles according to the present embodiment, surface portion of a hydrous gel is preferably crosslinked (post-crosslinked) using a crosslinking agent. It is preferable that post-crosslinking is performed at the timing that the hydrous gel has a specific water content. The timing for the post-crosslinking is preferably a time point at which the water content of the hydrous gel is 10% to 60% by mass, more preferably a time point at which the water content of the hydrous gel is 20% to 55% by mass, and still preferably a time point at which the water content of the hydrous gel is 30% to 50% by mass.

Examples of the post-crosslinking agent for performing post-crosslinking include compounds having two or more reactive functional groups. Examples of the compounds include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromhydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(O-hydroxyethyl)]adipamide. Among these, the polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are more preferable. These post-crosslinking agents may be used alone or in combination of two or more kinds thereof.

The amount of the post-crosslinking agent cannot be absolutely determined since it varies depending on the type of the post-crosslinking agent, but the amount is usually a ratio of 0.00001 to 0.02 mol, preferably 0.0001 to 0.01 mol, and more preferably 0.0005 to 0.005 mol, in terms of a ratio with respect to 1 mol of the water-soluble ethylenically unsaturated monomers used for polymerization.

From the viewpoint of sufficiently increasing the crosslinking density in a surface portion of the water-absorbent resin particles to enhance the gel strength of the water-absorbent resin particles, the amount of the post-crosslinking agent to be used is preferably 0.00001 mol or more, and from the viewpoint of increasing the water retention capacity of the water-absorbent resin particles, the amount is preferably 0.02 mol or less.

A dried product of the surface-crosslinked water-absorbent resin particles can be obtained by distilling off water and the hydrocarbon dispersion medium by known methods after the post-crosslinking reaction.

The water-absorbent resin particles according to the present embodiment can be used in mixture with, for example, a gel stabilizer, a metal chelating agent, silica, or the like. The water-absorbent resin particles according to the present embodiment can be made to have a desired particle size distribution at the time of point obtained by the above-mentioned production method, but the particle size distribution may be set to a predetermined particle size distribution by further performing operations such as adjustment of a particle size through classification with a sieve.

The water-absorbent resin particles according to the present embodiment can have a median particle diameter of, for example, 250 to 850 μm, and is preferably 300 to 700 μm, and more preferably 300 to 500 μm.

The water-absorbent resin particles generally take shapes such as a substantial spherical shape, a crushed shape, a granular shape, and aggregates thereof depending on a production process thereof. From the viewpoint that the effect of the present invention is more easily obtained, the water-absorbent resin particles according to the present embodiment may be, for example, in a granular shape. The granular shape in the present specification indicates that particles have a number of projections on surfaces thereof and can also be mentioned as a fine uneven shape. The water-absorbent resin particles according to the present embodiment may also be aggregates of granular particles.

The water-absorbent resin particles according to the present embodiment have a high water absorption capacity even with respect to physiological saline. The water retention capacity of the physiological saline of the water-absorbent resin particles according to the present embodiment can be, for example, 10 to 25 g/g or 15 to 25 g/g. Incidentally, the water absorption rate of physiological saline of the water-absorbent resin particles according to the present embodiment can be, for example, 10 seconds or less, and may also be 8 seconds or less, or 6 seconds or less. The water retention capacity of the physiological saline and the water absorption rate of physiological saline are measured by methods described in Examples which will be described later.

The water-absorbent resin particles according to the present embodiment preferably have an artificial menstrual blood absorption rate of 10 seconds or less. The artificial menstrual blood absorption rate may be 8 seconds or less, or 7 seconds or less. The artificial menstrual blood absorption rate can be, for example, 1 second or more, or 3 seconds or more. The artificial menstrual blood absorption rate is measured according to the method described in Examples which will be described later.

The water-absorbent resin particles according to the present embodiment are excellent in absorbing a solid component-containing viscous liquid such as blood, and thus, they can be applied in the fields of, for example, disposable blood absorbent articles such as sanitary napkins and tampons, medical blood absorbent articles, wound-protecting agents, wound-treating agents, surgical drainage treatment agents, disposable paper diapers, and the like.

In particular, for feminine sanitary napkins, it is possible to quickly absorb the moisture in the menstrual blood by using the water-absorbent resin particles according to the present embodiment, and it is possible to expect a further reduction in the leakage of menstrual blood since the volume of the water-absorbing resin particles is significantly increased after absorption, and thus, the adhesiveness between a product and a portion near the vaginal opening in the body is increased even in a case of thin sanitary napkins.

The water-absorbent resin particles according to the present embodiment can be suitably used for absorbent materials. The absorbent materials may include, for example, water-absorbent resin particles and fibrous materials.

The mass ratio of the water-absorbent resin particles in the absorbent material can be 2% to 60%, and is preferably 10% to 30%, with respect to total amount of the water-absorbent resin particles and the fibrous materials. The structure of the absorbent material can be, for example, in a form in which water-absorbent resin particles and the fibrous materials are uniformly mixed, or may be in a faun in which water-absorbent resin particles are held between fibrous materials formed in the sheet shape or layer shape, or in other forms.

Examples of the fibrous material include cellulose-based fibers such as finely pulverized wood pulp, cotton, cotton linter, rayon, and cellulose acetate, and synthetic fibers such as polyamides, polyesters, and polyolefins. In addition, the fibrous materials may be a mixture of the above-mentioned fibers.

Individual fibers may be bonded together by adding an adhesive binder to the fibrous materials in order to enhance the shape retention properties before and during use of the absorbent materials. Examples of such adhesive binder include hot-melt synthetic fibers, hot-melt adhesives, and adhesive emulsions.

Examples of such hot-melt synthetic fibers include full-melt type binders such as polyethylene, polypropylene, and an ethylene-propylene copolymer; and non-full-melt type binders formed of polypropylene and polyethylene in a side-by-side or core-and-sheath configuration. In the above-mentioned non-full-melt type binders, the polyethylene portion alone is hot-melted. Examples of the hot-melt adhesive include blends of base polymers such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene, with a tackifier, a plasticizer, an antioxidant, and the like.

Examples of the adhesive emulsions include polymers of at least one or more monomers selected from a group consisting of methyl methacrylate, styrene, acrylonitrile, 2-ethylhexyl acrylate, butyl acrylate, butadiene, ethylene, and vinyl acetate. These adhesive binders may be used alone or in combination of two or more kinds thereof.

The absorbent article according to the present embodiment includes the above-mentioned water-absorbent resin particles. The absorbent article according to the present embodiment includes, for example, a liquid-permeable sheet, the absorbent material, and a liquid-impermeable sheet in this order. The absorbent article can be applied to, for example, disposable blood-absorbent articles such as sanitary napkins.

Examples of materials for the liquid-permeable sheets include non-woven fabrics formed of polyolefins such as polyethylene and polypropylene, polyesters, polyamides, and porous synthetic resin films or the like. Examples of materials for the liquid-impermeable sheets include synthetic resin films formed of polyethylene, polypropylene, ethylenevinylacetate, polyvinyl chloride, or the like; films formed of composites of these synthetic resins and nonwoven fabrics; and films formed of composites of these synthetic resins with woven fabrics. These liquid-impermeable sheets may also be endowed with vapor-transmitting properties.

The absorbent material and the absorbent article may further include amorphous silica, deodorants, antibacterial agents, fragrances, and the like.

EXAMPLES

Hereinafter, the present invention will be described in more detail with reference to Examples, but the present invention is not limited to these Examples.

[Evaluation Test on Water-Absorbent Resin Particles]

The water-absorbent resin particles obtained in Examples 1 to 3 and Comparative Examples 1 to 4 below were subjected to each test shown below and evaluated. Hereinafter, each of the evaluation test methods will be described.

(1) Preparation of Artificial Menstrual Blood

The respective following components were blended into ion exchanged water and dissolved therein such that NaCl was at 1.00% by mass, $Na_2CO_3$ was at 0.40% by mass, glycerin was at 10.00% by mass, and carboxymethyl cellulose having a molecular weight of 25,000 was at 0.45% by mass to obtain an artificial test menstrual blood.

(2) Water Retention Capacity of Physiological Saline

A cotton bag (Cottonbroad No. 60, 100 mm in width×200 mm in length) into which 2.0 g of water-absorbent resin particles had been put was placed in a beaker having a capacity of 500 ml. 500 g of a 0.9%-by-mass aqueous sodium chloride solution (physiological saline) was poured into the cotton bag having the water-absorbent resin particles therein at once such that the powder was not aggregated, and the upper part of the cotton bag was closed with a rubber band and left to stand for 30 minutes so that the water-absorbent resin particles were swollen. The cotton bag after an elapse of 30 minutes was dehydrated for 1 minute using a dehydrator (manufactured by Kokusan Co., Ltd., product number: H-122) which had been set at a centrifugal force of 167 G and the mass Wa (g) of the cotton bag containing the swollen gel after dehydration was measured. The same operation was repeated while not adding the water-absorbent resin particles and the mass Wb (g) of the empty cotton bag upon wetting was measured, and the water retention capacity of physiological saline was calculated by the following equation:

$$\text{Water retention capacity of physiological saline (g/g)} = [Wa - Wb]/2.0$$

(3) Water Absorption Rate of Physiological Saline

The water absorption rate of physiological saline was measured in a room controlled to 25° C.±1° C. 50±0.1 g of physiological saline that had been put into a beaker having a capacity of 100 ml was adjusted to a temperature of 25° C.±0.2° C. in a thermostatic bath and then stirred at 600 rpm with a magnetic stirrer bar (8 φmmφ×30 mm without a ring) to generate a vortex. 2.0±0.002 g of water-absorbent resin particles were added into the physiological saline at once, and a time (sec) until the vortex disappeared and the liquid surface became flat after addition of the water-absorbent resin particles was measured. The time was taken as a water absorption rate of physiological saline of the water-absorbent resin particles.

(4) Artificial Menstrual Blood Absorption Rate

The artificial menstrual blood absorption rate was measured in the same operation as the physiological saline absorption rate, except that the artificial menstrual blood adjusted to 37° C.±1° C. was used instead of physiological saline as a test solution.

(5) Median Particle Diameter (Particle Size Distribution)

JIS standard sieves were sequentially assembled in order from the top down, with a sieve with a mesh size of 850 μM, a sieve with a mesh size of 500 μm, a sieve with a mesh size of 425 μm, a sieve with a mesh size of 300 μm, a sieve with a mesh size of 250 μm, a sieve with a mesh size of 180 μm, a sieve with a mesh size of 150 μm, and a receiving tray.

50 g of water-absorbent resin particles were fed to the topmost sieve of the combination and shaken for 20 minutes using a Ro-Tap type shaker to conduct classification. After the classification, the mass of the water-absorbent resin particles remaining on each sieve was calculated as a mass percentage with respect to the total amount to determine a particle size distribution. The calculated values on the sieves were integrated in descending order of the particle diameters with regard to the particle size distribution, and the relationship between the mesh size of the sieve and the integrated value of the mass percentages of the water-absorbent resin particles remaining on the sieve was plotted on a logarithmic probability paper. The plotted points on the probability paper were connected by straight lines, and thus, the particle diameter corresponding to 50% by mass of the integrated mass percentage was taken as a median particle diameter.

The presence ratio of the water-absorbent resin particles having a particle diameter of more than 250 μm and 850 μm or less is a sum of the ratios of the water-absorbent resin particles remaining on the sieves having mesh sizes of 500 μm, 425 μm, 300 μm, and 250 μm, and similarly, the presence ratio of the water-absorbent resin particles having a particle diameter of 250 μm or less is a numerical value obtained by adding up all the ratios of the water-absorbent resin particles remaining on the sieves having mesh sizes of 180 μm and 150 μm, and the receiving tray.

(6) Artificial Menstrual Blood Swelling Test 1.0 g of water-absorbent resin particles were weighed and put into a measuring cylinder (scale of 1 ml) with an inner diameter of 27 mm and a capacity of 100 ml, and disposed such that the water-absorbent resin particles became uniform in the cylinder. Thereafter, 10 ml of artificial menstrual blood (with the density of artificial menstrual blood being 1.03 g/cm$^3$) was injected into the cylinder at once. At a time point after an elapse of 60 seconds or 300 seconds from the injection, a highest point in the volumes of the swollen water-absorbent resin particles was measured and the numerical value was read in a 1-ml unit and taken as a volume (ml) after swelling. An artificial menstrual blood volume increase rate was calculated according to Equation (I) below.

Artificial menstrual blood volume increase rate (%)= $(A-B)/B \times 100$     (I), A . . . Volume (ml) after swelling
B . . . Volume (ml) of injected artificial menstrual blood The results are shown in Table 2 and FIG. 1. In FIG. 1, (1), (2), and (3) represent the water-absorbent resin particles after swelling in the artificial menstrual blood swelling tests in Example 1, Comparative Example 1, and Comparative Example 2, respectively.

(7) Pure Water Swelling Test

By the same operation as in the artificial menstrual blood swelling test, except that pure water was used instead of the artificial menstrual blood as a test solution and the injection amount was changed to 30 ml, a pure water volume increase rate was determined. The results are shown in Table 2.

Example 1

A cylindrical round-bottomed separable flask including sidewall baffles at four positions (baffle width: 7 mm) with an inner diameter of 110 mm and a capacity of 2 L, which was equipped with a reflux condenser, a dropping funnel, and a nitrogen gas introduction tube, and a stirrer having stirring blades including two sets of four inclined paddle blades (surface-treated with a fluororesin) with a blade diameter of 50 mm, was prepared. 660 ml of n-heptane as a petroleum-based hydrocarbon dispersion medium was put into the flask, 0.984 g of sorbitan monolaurate (trade name: Nonion LP-20R, HLB value of 8.6, manufactured by NOF Corporation) was added thereto, and the mixture was heated to 50° C. Sorbitan monolaurate was dissolved in n-heptane by heating, and then the internal temperature was lowered to 40° C.

92 g (1.02 mol) of a 80%-by-mass aqueous acrylic acid solution was put into an Erlenmeyer flask having a capacity of 500 ml, and 146 g of a 21%—by mass aqueous sodium hydroxide solution was added dropwise thereto under ice-cooling from the external side to perform neutralization of 75 mol % with respect to acrylic acid. Next, 0.101 g (0.374 mmol) of potassium persulfate as a radical polymerization initiator was added to the partially neutralized aqueous acrylic acid solution thus obtained, thereby preparing an aqueous monomer solution.

The aqueous monomer solution was added to the separable flask, and after the inside of the system was sufficiently replaced with nitrogen, a rotational speed of the stirrer was set to 700 rpm, and the flask was immersed in a water bath at 70° C. and maintained for 60 minutes.

Thereafter, 0.092 g of amorphous silica (Carplex #80, manufactured by Evonik Degussa Japan, Inc.) as a powdery inorganic flocculating agent, which had been dispersed in 100 g of n-heptane in advance, was added to the polymerization solution containing the produced hydrous gel, n-heptane, and a surfactant, and mixed for 10 minutes. Then, the flask containing the reaction solution was immersed in an oil bath at 125° C., and 104 g of water was extracted out of the system while n-heptane was refluxed by azeotropic distillation with n-heptane and water. Then, 8.28 g (0.95 mmol) of a 2%-by-mass aqueous ethylene glycol diglycidyl ether solution as a post-crosslinking agent was added thereto and the mixture was maintained at an internal temperature of 80° C.±2° C. for 2 hours.

Thereafter, n-heptane was evaporated and the residue was dried to obtain a dried product. The dried product was passed through a sieve having a mesh size of 850 μm to obtain 90.5 g of water-absorbent resin particles. The obtained water-absorbent resin particles were in the form in which granular (fine uneven) particles were aggregated. The obtained water-absorbent resin particles were evaluated according to the above-mentioned each test method.

Example 2

A cylindrical round-bottomed separable flask including sidewall baffles at four positions (baffle width: 7 mm) with an inner diameter of 110 mm and a capacity of 2 L, which was equipped with a reflux condenser, a dropping funnel, and a nitrogen gas introduction tube, and a stirrer having stirring blades including two sets of four inclined paddle blades (surface-treated with a fluororesin) with a blade diameter of 50 mm, was prepared. 660 ml of n-heptane as a petroleum-based hydrocarbon dispersion medium was put into the flask, 1.10 g of sorbitan monolaurate (trade name: Nonion LP-20R, HLB value of 8.6, manufactured by NOF Corporation) was added thereto, and the mixture was heated to 50° C. Sorbitan monolaurate was dissolved in n-heptane by heating, and then the internal temperature was lowered to 40° C.

92 g (1.02 mol) of a 80%-by-mass aqueous acrylic acid solution was put into an Erlenmeyer flask having a capacity of 500 ml, and 146.0 g of a 21%—by mass aqueous sodium hydroxide solution was added dropwise thereto under ice-cooling from the external side to perform neutralization of 75 mol % with respect to acrylic acid. Next, 0.101 g (0.374 mmol) of potassium persulfate as a radical polymerization initiator was added to the partially neutralized aqueous acrylic acid solution thus obtained, thereby preparing an aqueous monomer solution.

The aqueous monomer solution was added to the separable flask, and after the inside of the system was sufficiently replaced with nitrogen, a rotational speed of the stirrer was set to 700 rpm, and the flask was immersed in a water bath at 70° C. and maintained for 60 minutes. 0.41 g (0.047 mmol) of a 2%-by-mass aqueous ethylene glycol diglycidyl ether solution as an intermediate-crosslinking agent was added thereto and the mixture was maintained at 75° C. for 30 minutes.

Thereafter, 0.092 g of amorphous silica (Carplex #80, manufactured by Evonik Degussa Japan, Inc.) as a powdery inorganic flocculating agent was added to the polymerization solution containing the produced hydrous gel, n-heptane, and a surfactant under stirring, and sufficiently mixed. Then, the flask containing the reaction solution was immersed in an oil bath at 125° C., and 109 g of water was extracted out of the system while n-heptane was refluxed by azeotropic distillation with n-heptane and water. Then, 24.84 g (2.85 mmol) of a 2%-by-mass aqueous ethylene glycol diglycidyl ether solution as a post-crosslinking agent was added thereto and the mixture was maintained at an internal temperature of 80° C.±2° C. for 2 hours.

Thereafter, n-heptane was evaporated and the residue was dried to obtain a dried product. The dried product was passed through a sieve having a mesh size of 850 μm to obtain 90.3 g of water-absorbent resin particles. The obtained water-absorbent resin particles were evaluated according to the above-mentioned each test method.

Example 3

The same treatment as in Example 2, except that in Example 3, 111 g of water was extracted out of the system while n-heptane was refluxed by azeotropic distillation with n-heptane and water, and the amount of a 2%-by-mass aqueous ethylene glycol diglycidyl ether solution as a post-crosslinking agent to be added was changed to 41.40 g (4.75 mmol), was performed to obtain 88.9 g of water-absorbent resin particles. The obtained water-absorbent resin particles were evaluated according to the above-mentioned each test methods.

Comparative Example 1

70 g of a 80%-by-mass aqueous acrylic acid solution was put into an Erlenmeyer flask having a capacity of 500 ml, and 111.1 g of a 21%-by-mass aqueous sodium hydroxide solution was added dropwise thereto under ice-cooling to perform neutralization of 75 mol % with respect to acrylic acid. Next, 0.084 g of potassium persulfate as a radical polymerization initiator was added to the partially neutralized aqueous acrylic acid solution thus obtained.

550 ml of n-heptane as a petroleum-based hydrocarbon dispersion medium and 0.84 g of sorbitan monolaurate (trade name: Nonion LP-20R, HLB value of 8.6, manufactured by NOF Corporation) as a surfactant were added into a cylindrical four-necked, round-bottomed flask with a capacity of 1.5 L, which was equipped with a stirrer, a reflux condenser, a dropping funnel, and a nitrogen gas introduction tube, and the mixture was heated to 50° C. Sorbitan monolaurate was dissolved in n-heptane by heating, and then the internal temperature was lowered to 40° C. Next, the above-mentioned partially neutralized acrylic acid aqueous solution was added thereto to prepare a reverse-phase suspension, and after the inside of the system was replaced with nitrogen, a rotational speed of the stirrer was set to 700 rpm, and the flask was immersed in a water bath at 70° C. and maintained for 3 hours.

Thereafter, water was removed out of the azeotropic mixture of n-heptane and water by reheating. Then, 0.2 g of ethylene glycol diglycidyl ether as a surface crosslinking agent was added thereto to perform a crosslinking reaction. After the crosslinking reaction, the mixture was dried by distilling off n-heptane and water in the system and passed through a sieve having a mesh size of 850 μm to obtain 70.3 g of water-absorbent resin particles. The obtained water-absorbent resin particles were evaluated according to the above-mentioned each test method.

Comparative Example 2

The same treatment as in Example 2, except that 129 g of water was extracted out of the system while n-heptane was refluxed by azeotropic distillation with n-heptane and water, and then the amount of a 2%-by-mass aqueous ethylene glycol diglycidyl ether solution as a post-crosslinking agent to be added was changed to 4.14 g (0.48 mmol), was performed to obtain 90.0 g of water-absorbent resin particles. The obtained water-absorbent resin particles were evaluated according to the above-mentioned each test method.

Comparative Example 3

The same treatment as in Example 2, except that 91 g of water was extracted out of the system while n-heptane was refluxed by azeotropic distillation with n-heptane and water, and then the amount of a 2%-by-mass aqueous ethylene glycol diglycidyl ether solution as a post-crosslinking agent to be added was changed to 4.14 g (0.48 mmol), was performed to obtain 90.3 g of water-absorbent resin particles. The obtained water-absorbent resin particles were evaluated according to the above-mentioned each test method.

Comparative Example 4

The same treatment as in Example 2, except that a powdery inorganic flocculating agent was not added after the intermediate crosslinking reaction, the reaction solution was warmed in an oil bath at 125° C., 125 g of water was extracted out of the system while n-heptane was refluxed by azeotropic distillation with n-heptane and water, and then 16.56 g (1.90 mmol) of a 2%-by-mass aqueous ethylene glycol diglycidyl ether solution as a post-crosslinking agent was added, was performed to obtain 88.9 g of water-absorbent resin particles. The obtained water-absorbent resin particles were evaluated according to the above-mentioned each test method.

TABLE 1

|  | Water retention capacity of physiological saline (g/g) | Physiological saline absorption rate (g/g) | Artificial menstrual blood absorption rate (sec) | Particle size distribution | | Median particle diameter (μm) |
|---|---|---|---|---|---|---|
|  |  |  |  | more than 250 μm and 850 μm or less(%) | 250 μm or less (%) |  |
| Example 1 | 18 | 4 | 6 | 91 | 9 | 420 |
| Example 2 | 20 | 4 | 6 | 94 | 6 | 397 |
| Example 3 | 19 | 4 | 4 | 83 | 17 | 351 |
| Comparative Example 1 | 21 | 2 | 4 | 24 | 76 | 199 |
| Comparative Example 2 | 38 | 4 | 7 | 92 | 8 | 369 |
| Comparative Example 3 | 22 | 2 | 4 | 81 | 19 | 330 |
| Comparative Example 4 | 23 | 2 | 4 | 57 | 43 | 266 |

TABLE 2

|  | Liquid to be absorbed: pure water | | | | Liquid to be absorbed: artificial menstrual blood | | | |
|---|---|---|---|---|---|---|---|---|
|  | Swollen volume (ml) | | Volume increase rate (%) | | Swollen volume (ml) | | Volume increase rate (%) | |
|  | 60-sec value | 300-sec value | 60-sec value | 300-sec value | 60-sec value | 300-sec value | 60-sec value | 300-sec value |
| Example 1 | 63 | 65 | 110 | 117 | 20 | 22 | 100 | 120 |
| Example 2 | 57 | 61 | 90 | 103 | 22 | 24 | 120 | 140 |
| Example 3 | 57 | 61 | 90 | 103 | 22 | 24 | 120 | 140 |
| Comparative Example 1 | 57 | 61 | 90 | 103 | 15 | 17 | 50 | 70 |
| Comparative Example 2 | 32 | 32 | 7 | 7 | 12 | 12 | 20 | 20 |
| Comparative Example 3 | 49 | 53 | 63 | 77 | 15 | 16 | 50 | 60 |
| Comparative Example 4 | 50 | 52 | 67 | 73 | 15 | 16 | 50 | 60 |

As shown in Table 2, the volume increase rates of the water-absorbent resin particles obtained in Examples were high, and among those, the volume increase rates in a case of absorption of the artificial menstrual blood were good.

[Evaluation of Absorbent Article]

(1) Preparation of Absorbent Material and Absorbent Article

Absorbent materials and absorbent articles were prepared using the water-absorbent resin particles obtained in Examples 1 to 3 and Comparative Examples 1 to 4. 0.48 g of water-absorbent resin particles and 1.92 g of shredded pulp (Rayfloc, manufactured by Rayonier) were used and uniformly mixed by an air sheet-making technique to prepare a sheet-like absorbent material core having a size of 20 cm×6 cm. Next, an absorbent material was prepared by pressing the absorbent material core while sandwiching the core between two pieces of tissue paper, each of which had the same size as the absorbent material core and a basis weight of 16 g/m² by the application of a load of 196 kPa for 30 seconds to the entire of the core. Furthermore, an air-through type porous liquid-permeable sheet which was made of polyethylene-polypropylene and had a basis weight of 22 g/m² was disposed on the upper surface of the absorbent material, a liquid-impermeable sheet which was made of polyethylene and had the same size and basis weight was disposed on the lower surface of the absorbent material, and then the absorbent material was sandwiched therebetween to obtain an absorbent article having a basis weight of water-absorbent resin particles of 40 g/m² and a basis weight of hydrophilic fibers of 160 g/m².

(2) Test Blood

As a test blood, a horse defibrinated blood (hematocrit value of 40%, manufactured by Nippon Biotest Laboratories Inc.) was used.

(3) Blood Infiltration Test (Absorbent Material)

First, an absorbent article was placed on a horizontal platform. A measurement device provided with a liquid-injection cylinder having an internal diameter of 2 cm was placed at the central portion of the absorbent article, 7 ml of a test blood was poured into the cylinder at once, and a time required for the test blood in the cylinder from the introduction of the blood to complete disappearance was measured using a stopwatch and taken as a first blood infiltration rate (sec). At 10 minutes after the first introduction of the test blood, 7 ml of the test blood was introduced to the cylinder again and the same operation was performed to measure the second blood infiltration rate (sec). The results are shown in Table 3.

TABLE 3

|  | Blood infiltration test (absorbent material) Horse defibrinated blood with a hematocrit value of 40% Blood infiltration rate (sec) | | |
|---|---|---|---|
|  | First | Second | Total |
| Example 1 | 31 | 94 | 125 |
| Example 2 | 33 | 84 | 117 |
| Example 3 | 31 | 83 | 114 |
| Comparative Example 1 | 39 | 130 | 169 |
| Comparative Example 2 | 39 | 127 | 166 |
| Comparative Example 3 | 35 | 121 | 156 |
| Comparative Example 4 | 45 | 130 | 175 |

As shown in the results in Table 3, the absorbent articles using the water-absorbent resin particles obtained in Examples 1 to 3 had good blood infiltration rates, and in particular, excellent blood infiltration rates in the second measurement, as compared with the absorbent articles prepared using the water-absorbent resin particles obtained in Comparative Examples.

The invention claimed is:

1. Water-absorbent resin particles comprising a cross-linked polymer comprising a monomer unit derived from a water-soluble ethylenically unsaturated monomer, wherein an artificial menstrual blood volume increase rate as measured in an artificial menstrual blood swelling test conducted in the following order of i), ii), and iii) is 70% or more:
  i) putting 1.0 g of water-absorbent resin particles into a measuring cylinder with an inner diameter of 27 mm,
  ii) injecting 10 ml of artificial menstrual blood into the cylinder at once to swell the water-absorbent resin particles, and
  iii) measuring, a volume (A) of the swollen water-absorbent resin particles after an elapse of 60 seconds from the injection and calculating an artificial menstrual blood volume increase rate according to Equation (I) below:

Artificial menstrual blood volume increase rate (%)=(A-B)/B×100 ... (I)
  A ... Volume (ml) of swollen water-absorbent resin particles
  B ... Volume (ml) of injected artificial menstrual blood.

2. The water-absorbent resin particles according to claim 1, wherein a ratio of particles having a particle diameter of more than 250 μm and 850 μm or less is 70% by mass or more and a ratio of particles having a particle diameter of 250 μm or less is 20% by mass or less, with respect to the total amount of the water-absorbent resin particles.

3. The water-absorbent resin particles according to claim 1, wherein an artificial menstrual blood absorption rate is 10 seconds or less.

4. The water-absorbent resin particles according to claim 1, wherein a water retention capacity of physiological saline is 10 to 25 g/g.

5. An absorbent article comprising the water-absorbent resin particles according to claim 1.

* * * * *